(12) United States Patent
Gill

(10) Patent No.: US 8,128,600 B2
(45) Date of Patent: Mar. 6, 2012

(54) CATHETER AND GUIDE TUBE FOR INTRACEREBRAL APPLICATION

(75) Inventor: Steven Streatfield Gill, Bristol (GB)

(73) Assignee: Renishaw (Ireland) Limited, Swords (IE)

( * ) Notice: Subject to any disclaimer, the term of this patent is extended or adjusted under 35 U.S.C. 154(b) by 1039 days.

(21) Appl. No.: 10/505,240

(22) PCT Filed: Mar. 11, 2003

(86) PCT No.: PCT/GB03/01030
§ 371 (c)(1),
(2), (4) Date: Feb. 22, 2005

(87) PCT Pub. No.: WO03/077785
PCT Pub. Date: Sep. 25, 2003

(65) Prior Publication Data
US 2005/0154297 A1    Jul. 14, 2005

(30) Foreign Application Priority Data
Mar. 12, 2002   (GB) .................. 0205772.7

(51) Int. Cl.
*A61M 5/32* (2006.01)
*A61B 17/04* (2006.01)
*A61B 17/80* (2006.01)
*A61F 2/08* (2006.01)

(52) U.S. Cl. .................. 604/175; 606/300; 606/305

(58) Field of Classification Search .......... 604/174–178, 604/180, 93.01, 284, 8, 9, 19, 164.04; 606/72, 606/73, 75, 300–308, 319
See application file for complete search history.

(56) References Cited

U.S. PATENT DOCUMENTS

| | | | | |
|---|---|---|---|---|
| 5,951,539 A * | 9/1999 | Nita et al. | ....... | 604/526 |
| 6,045,532 A * | 4/2000 | Eggers et al. | ....... | 604/114 |
| 6,267,769 B1 | 7/2001 | Truwit | | |
| 6,517,550 B1 * | 2/2003 | Konya et al. | ....... | 606/113 |
| 6,591,472 B1 * | 7/2003 | Noone et al. | ....... | 29/417 |
| 6,609,020 B2 * | 8/2003 | Gill | ....... | 600/423 |
| 6,719,727 B2 * | 4/2004 | Brimhall et al. | ....... | 604/177 |
| 6,902,569 B2 * | 6/2005 | Parmer et al. | ....... | 606/108 |
| 7,033,326 B1 * | 4/2006 | Pianca et al. | ....... | 600/585 |
| 2001/0001117 A1 | 5/2001 | Chow | | |
| 2001/0003156 A1 * | 6/2001 | Gill | ....... | 606/130 |
| 2001/0027599 A1 | 10/2001 | Elsberry | | |
| 2001/0056275 A1 | 12/2001 | Brushey | | |

FOREIGN PATENT DOCUMENTS
WO    WO 00/69502 A    11/2000

OTHER PUBLICATIONS

Oct. 24, 2010 Search Report issued in EP Application No. EP 10 01 0990.9.
Oct. 24, 2010 Office Action issued in EP Application No. EP 10 01 0990.9.

* cited by examiner

*Primary Examiner* — Matthew F Desanto
(74) *Attorney, Agent, or Firm* — Oliff & Berridge, PLC

(57) ABSTRACT

A catheter for use in neurosurgery, and a method of positioning neurosurgical apparatus. The catheter has a fine tube arranged for insertion into the brain parenchyma of a patient with an external diameter of not more than 1.0 mm. The catheter and method may be used in stereotactically targeting treatment of abnormalities of brain function, and for the infusion of therapeutic agents directly into the brain parenchyma. This is advantageous when a therapeutic agent would have widespread unwanted effects which could be avoided by confining the delivery to the malfunctioning or damaged brain tissue.

2 Claims, 5 Drawing Sheets

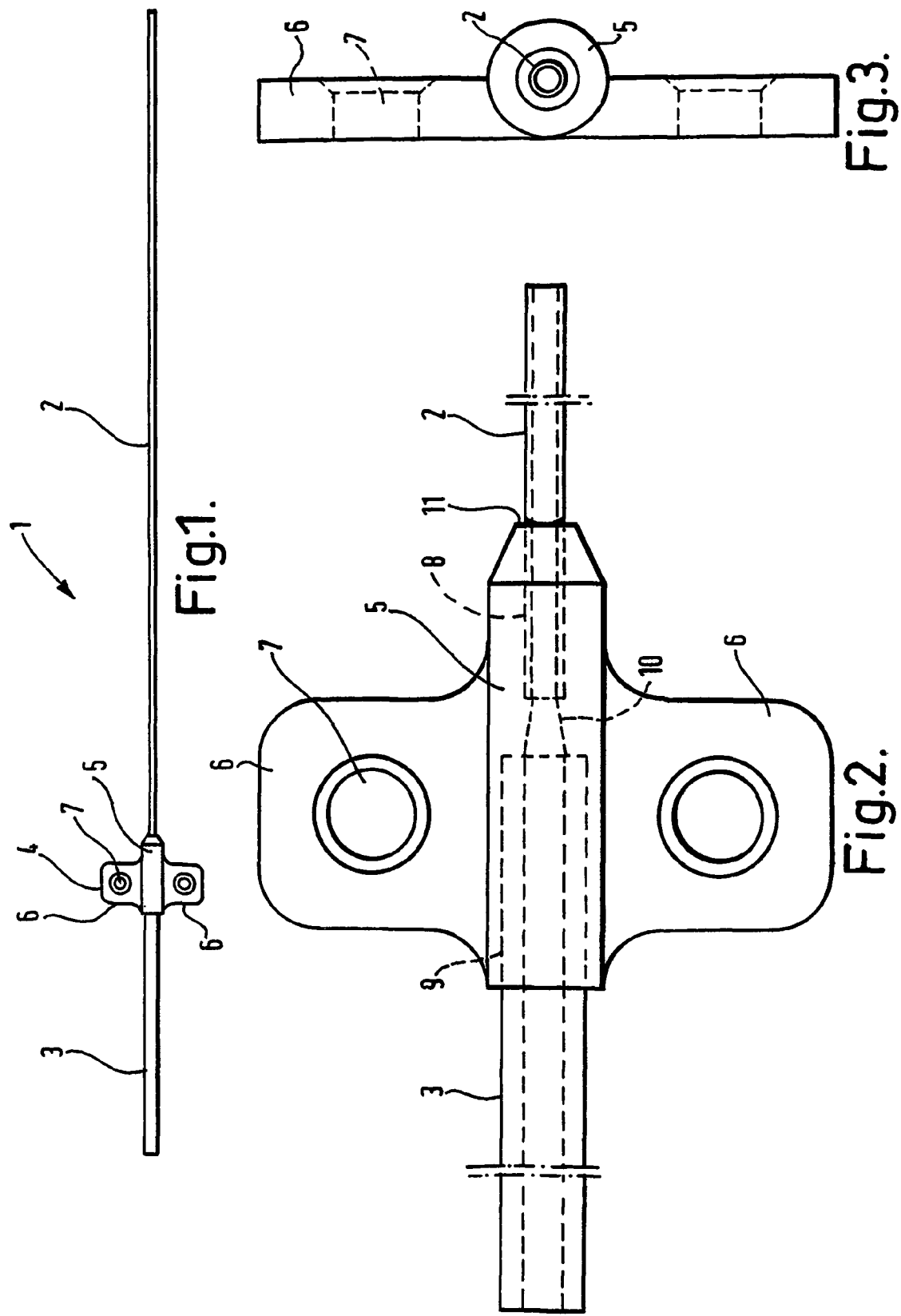

CATHETER AND GUIDE TUBE FOR INTRACEREBRAL APPLICATION

CROSS-REFERENCE TO RELATED APPLICATIONS

This patent application is a National Phase filing of PCT/GB03/01030, filed Mar. 11, 2003, which claims the benefit of priority of Great Britain Patent Application Serial No 0205772.7, filed Mar. 12, 2002, all of which are incorporated herein by reference.

TECHNICAL FIELD

The present invention relates to apparatus for use in neurosurgery, and to a method of positioning neurosurgical apparatus. The apparatus and method are particularly useful in stereotactically targeting treatment of abnormalities of brain function, and for the infusion of therapeutic agents directly into the brain parenchyma. This would be particularly useful when a therapeutic agent given systemically will have widespread unwanted side effects which would be avoided by confining the delivery to the malfunctioning or damaged brain tissue.

BACKGROUND OF THE INVENTION

Examples of treating abnormalities of brain function include the acute infusion of Gamma-amino-buturic-acid agonists into an epileptic focus or pathway to block transmission, and the chronic delivery of opiates or other analgesics infused directly to the peri-aqueductal grey matter or to thalamic targets for the treatment of intractable pain. Also, cytotoxic agents can be delivered directly into a brain tumor. Intraparenchymal infusion could also be used to deliver therapeutic agents to brain targets that could not be delivered systemically because they will not cross the blood-brain barrier. For example, the treatment of patients with Parkinson's disease, Alzheimer's disease, head injury, stroke and multiple sclerosis may be carried out by the infusion of neurotrophic factors to protect and repair failing or damaged nerve cells. Neurotrophins may also be infused to support neural grafts transplanted into damaged or malfunctioning areas of the brain in order restore function.

Intraparenchymal drug delivery has been demonstrated in non human primates and in rats. For intraparenchymal drug delivery to a human or non-human brain, it is proposed that a catheter be implanted, and the drug be pumped intermittently or continuously to the desired brain target. For long term drug delivery, a pump containing a reservoir would be implanted subcutaneously and the reservoir refilled as necessary percutaneously through a palpable port. In particular U.S. Pat. No. 6,042,579 discloses techniques for treating neurodegenerative disorders by the infusion of nerve growth factors into the brain.

In order to perform neurosurgery, the surgeon needs, in the first instance, to identify the position of the desired target. This is normally achieved by fixing a stereotactic reference frame to the patient's head which can be seen on diagnostic images, and from which measurements can be made. The stereotactic frame then acts as a platform from which an instrument is guided to a desired target using a stereoguide that is set to the measured co-ordinates. Once an instrument is guided to the desired target, treatment can begin.

A number of difficulties are encountered in such neurosurgical procedures. Sub-optimal placement of the instrument being inserted may lead to significant morbidity or treatment failure. Brain targets for treating functional disorders are usually deeply situated and have small volumes. For example, a desired target for treating Parkinson's disease is situated in the sub-thalamic nucleus and is 3-4 mm in diameter, or an ovoid of 3-4 mm in diameter and 5-6 mm in length. Other targets such as the globus palladus or targets in the thalamus are usually no more than 1-2 mm larger. For such a small target sub-optimal placement of as little as 1 mm will not only reduce the effectiveness of the treatment, but may also induce unwanted side affects such as weakness, altered sensation, worsened speech and double vision. However, functional neurosurgical targets are often difficult or impossible to visualize on diagnostic images, and so that actual position may be need to be inferred with the reference to visible landmarks in the brain and using a standard atlas of the brain to assist the process. Anatomical variations between an individual and the atlas, and even between different sides of the same brain of an individual means that placement may be sub-optimal. Other reasons for sub-optimal placement may result from patient movement during image acquisition, or geometric distortion of imaging which can be intrinsic to the images method. Also, during surgery, brain shift can occur which might result from the change in the head position from that during image acquisition to the position on the operating table, from leakage of cerebrospinal fluid when a burr hole is made with a subsequent sinking of the brain, and also from the passage of the instrument through the brain. Surgeons attempt to correct these errors by performing electrophysiological studies on the patient undergoing functional neurosurgery, kept awake during the procedures.

Intraparenchymal catheters may be guided to their targets in the brain using stereotactic techniques. Typically, stereotactic localization of a brain target is accomplished by fixing the stereotactic base ring to the skull and identifying the position of the target using imaging techniques. The position of the target is identified using three dimension co-ordinates by making measurements from radio-opaque fiducials attached to the stereotactic base ring. The stereotactic base ring may then be used as a platform from which to guide instruments to the target using a stereoguide on the stereotactic base ring that is set to the measured co-ordinates. The catheter may then be guided towards the target through the brain tissue after rigidifying it by the insertion of a stiff wire through its bore. Alternatively, a straight wire may be guided to the target first, and the catheter introduced around the wire so that one end (i.e. the inserted or distal end) is located within the brain, and the opposite end (i.e. the external or proximal end) remains outside the brain. Once positioned, the external end of the catheter can be fixed to the skull, and connected to a pump whereby the therapeutic agent may be administered. It will be appreciated that the outer diameter of the catheter tubing should be as small as possible, particularly when especially sensitive parts of the brain are to be treated, such as the mesencephalic targets, and are therefore to be passed through by the catheter. Such highly sensitive regions of the brain tend to be located in deep positions typically between 70 and 100 mm from the surface of the skull, such as the brain stem. Of course, the thinner the catheter tubing, the greater the deflection during insertion to those deep targets within the brain, and the increased likelihood that placement will be sub-optimal.

SUMMARY OF THE INVENTION

The present invention seeks to optimize the placement of the catheter whilst minimizing the trauma to the brain by utilizing small diameter catheter tubing.

According to a first aspect of the invention there is provided a neurosurgical catheter having a fine tube arranged for insertion into the brain of a patient with an external diameter of not more than 1.0 mm. It is preferred that the external diameter of the catheter is not more than 0.7 mm, and even more preferred that it is not more than 0.65 mm. Most preferably, its external diameter if not more than 0.5 mm. The catheter is preferably generally circular in cross section.

It is also preferred that the catheter is a deep target neurosurgical catheter and has a length of at least 40 mm, more preferably at least 70 mm and most preferably at least 90 mm.

Since the fine tube is so fine, it is desirable for the catheter to further comprise a connector tube connected to one end of the fine tube, the connector tube being of greater diameter than the fine tube. Preferably the connector tube has an outer diameter of about 2 mm. Connection may be achieved by the inclusion of a hub disposed between the fine tube and the connector tube. According to a preferred embodiment, the hub includes a passageway connecting the fine tube and the connector tube, the passageway including a first passage in which the fine tube is securely inserted, a second passage in which the connector tube is securely inserted and a further link passage disposed between the first and second passages.

In a preferred embodiment, the hub includes a cylindrical body and one or more flanges by which the hub can be secured to the skull of the patient. The hub may be secured using any fixing arrangement, including glue and screws. It is particularly preferred that each flange includes an internal surface defining a countersunk hole by which the hub can be secured to the skull of a patient by screws.

Preferably, the hub includes a stop surface adjacent to where the fine tube is secured to the hub. It is also preferred that the hub is tapered towards that stop.

According to a second aspect of the invention, there is provided a neurosurgical instrument comprising a tube for insertion into the brain of a patient towards a desired target, the tube having a distal end for insertion into the brain, a proximal end and a head disposed at the proximate end of the tube for attachment to the skull of the patient; and a catheter according to the present invention for insertion into the brain of the patient via the tube. Other advantageous or preferred features of the catheter are described above.

Preferably, the head of the guide tube includes an externally threaded surface for engagement with the skull of the patient via an acrylic cement. According to a preferred embodiment, the head includes a slotted dome structure, and the catheter has a hub having a stop at one end which abuts the dome structure once the fine tube has been inserted into the guide tube. The slot is preferably shaped such that, as the catheter is bent over in the slot, it resists kinking. The domed structure is preferably shaped such that, as the catheter is bent over in the slot with the stop abutting the domed surface, the distal end of the catheter will remain accurately located at its target. Reference is made to GB-A-2357700 which discloses a guide tube with a head having a domed structure, the disclosure of which is incorporated herein by reference.

According to a third aspect of the invention there is provided a neurosurgical guide device comprising a tube for insertion into the brain of a patient towards a desired target, the tube having distal end for insertion, an opposite proximal end and a head disposed at the proximate end of the tube for attachment to the skull of the patient, characterized in that the internal diameter of the tube is not more than 1 mm; wherein the tube is of a length such that the distal end falls short of the target by between 1 and 20 mm. Preferably the length is such that the distal end falls short by between 5 and 10 mm.

According to a fourth aspect of the invention, there is provided a method of positioning a catheter at a target in the brain of a patient comprising; inserting a neurosurgical guide tube according to the third aspect of the present invention into the brain towards the target, wherein the distal end falls short of the target by between 5 and 20 mm; securing the head of the guide device to the skull; and inserting a catheter according to the present invention through the tube and to the target. It is preferred that the catheter is positioned at a deeply positioned target of at least 40 mm from the surface of the skull, more preferably at least 70 mm from the surface, and most preferably at least 90 mm from the surface of the skull.

The present application comprises a kit comprising:
one or more neurosurgical catheters according to the present invention;
one or more guide tubes for insertion into the brain of a patient towards a desired target, each tube having distal and proximate ends and a head disposed at the proximate end of the tube for attachment to the skull of the patient; and
one or more guide wires.

Preferably, the kit according is provided in a pack having separately marked sections, wherein each section contains one catheter, one guide tube and one guide wire. This enables each set of elements (i.e. the catheter, the guide tube and the guide wire) can be distinguished from other sets of the elements. This is important when different sets of elements are used on different sites of the brain.

BRIEF DESCRIPTION OF THE DRAWINGS

Embodiments of the present invention will be described by way of example only with reference to the accompanying drawings in which:

FIG. 1 is a view of a catheter according to the present invention;

FIG. 2 is a view showing part of the catheter of FIG. 1 with internal features shown in dotted lines;

FIG. 3 is an end view of the catheter from the right hand end of FIG. 2;

DETAILED DESCRIPTION OF THE INVENTION

Figure 4:
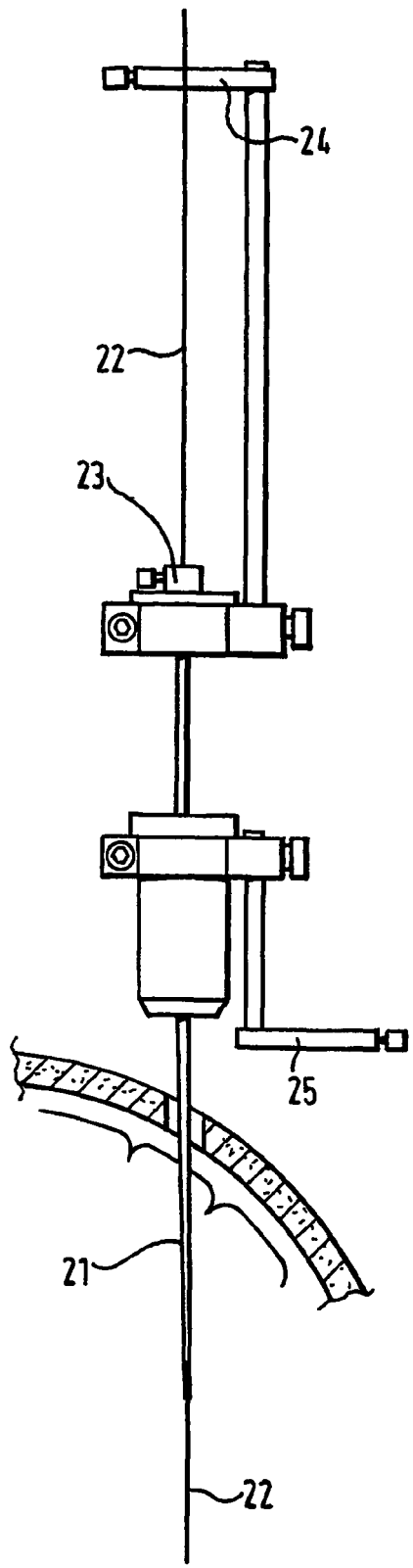
FIG. 4 shows a first phase of stereotactic insertion.

As explained above, insertion of a catheter into particularly sensitive regions of the brain leads to trauma on insertion which surgeons wish to minimize. The finer the catheter the less trauma the brain experiences. However, since the accuracy of insertion is crucially important, and since these particularly sensitive areas of the brain are a considerable distance from the skull surface, larger diameter catheters have been considered to be necessary in order to accurately place the distal end of the catheter. However, the present invention allows much finer catheters to be used.

Example 1

FIGS. 1,2 and 3 show a catheter 1 according to the present invention. The catheter 1 includes A length of fine tubing 2, the outer diameter which is no more than 1 mm, and most preferably no greater than 0.7 mm. It is even more preferred that the outer diameter be no more than 0.5 mm. In this instance, the catheter tubing 2 is constructed from polyurethane plastic and preferably from carbothane 55 DB20 (Thermedics Polymer Products, WOBURN MA, USA). The fine tubing 2 is linked to a length of connector tubing 3 having an outer diameter of about 2 mm, via a hub 4. The connector tubing 3 is, in this case, made from polyurethane plastic, such as carbothane 85AB20, although other materials could also be used.

The hub 4 in this case is also constructed using polyurethane, such as carbothane 72 DB20. Again, other materials may also be appropriate.

The fine tubing 2 is intended to be inserted into the brain of a patient, whereas the connector tubing 3 is intended to be connected to outflow tubing of a pump by which a therapeutic agent may be pumped intermittently or continuously to a desired brain target. For long term drug delivery, the pump would be implanted subcutaneously and the reservoir refilled as necessary percutaneously through a palpable port. In this case, the connector tubing 3 would be connected to outflow tubing of the pump which would be tunneled subcutaneously from the pump to the catheter. It's length will depend on particular installations and will be cut to length appropriately. The hub 4 includes a central body 5, which is generally cylindrical and a pair of diametrical opposing wings 6 each a containing a countersunk hole whereby the hub may be screwed to the outer surface of the skull of the patient.

The cylindrical body 5 of the hub 4 includes a passageway passing through its complete length. The passageway includes a first narrow passage 8 of uniform diameter into which the fine tubing is inserted and securely held. The passageway also includes a second wide passage 9 of uniform diameter into which the connector tubing 3 is inserted and securely held. Between the first and second passages 8,9 is a third linking passage 10 which is generally tapered in order to take account of the different internal diameters of the fine tubing 2 and the connector tubing 3. It will be noted that the ends of the third passage 10 are of the same or very similar diameter to the internal diameters of the fine tubing 2 and the connector tubing 3.

From FIG. 2, it can be seen that the right hand end of the hub 4 is frustoconical, and the end of the hub is planar and forms a stop 11, the significance of which will be understood from the description below.

Example 2

The insertion of the catheter will now be described. Firstly, a stereotactic frame is attached to the patient's skull and the position of the intracranial target is identified by imaging the patient wearing the stereotactic frame and defining the position of the target as three dimensional co-ordinates. This step is explained in more detail in the introduction to this patent specification and is a standard technique within the field of neurosurgery.

Once the target has been defined, a stereoguide is used which is set to the target coordinates. An appropriately sized guide tube having an internal diameter of no more that 1 mm is directed into the brain in the direction of the target. The guide tube is arranged with a head at one end, which, once inserted, can be attached to the patient's skull, for example by being bonded into a burrhole in the skull using an acrylic cement.

Before insertion, the guide tube is cut to a length short of the target, and sufficiently short that, while it passes through brain tissue, it does not enter those parts of the brain which are particularly sensitive to trauma. The distal end of the guide tube will typically fall several millimeters short of the target. The distance from the top of the head of the guide tube to the target is then measured, and a radio-opaque stylette is cut to length such that, when inserted down the guide tube it's distal end reaches the planned target. This means that the stylette will extend beyond the distal end of the guide tube.

The patient is then re-imaged in order to confirm the satisfactory placement of the stylette prior to removing the stylette and replacing it with the intraparenchymal catheter cut to the same length as the stylette. Again, the catheter will have an outer diameter of no more than one millimeter although it will be appreciated that the catheter, the stylette and the guide tube will all be matched so that the catheter and stylette will fit properly within the guide tube. If it is desired to use a very fine catheter of, say, 0.65 mm in outer diameter, an appropriate guide tube will also be used with an internal diameter of 0.75 mm.

When the catheter is inserted, it is expected that it will be reinforced during insertion by the location of a stiff wire through it's bore, most likely made from tungsten. Once the catheter has been inserted in the guide tube, the stop 11 on the hub 4 will abut the head of the guide tube meaning that the distal end of the catheter has reached the target. The stiff wire is removed, and the fine tubing 2 is bent through about 90° so that the hub 4 can be secured to the outer surface of the skull using screws passing through the countersunk holes 7. To facilitate the bending, the head of the guide tube is dome shaped and arranged such that, during bending, not only will the fine tubing 2 not kink, but also the distal end of the fine tubing will not move. This will be explained in more detail later in this specification.

The connector tubing 3 can then be connected to the outflow tubing of a pump. Generally, the connector tubing 3, will be tunneled SUBCUTANEOUSLY to the remotely positioned pump.

Example 3

In an alternative insertion technique, a number of phases or steps are taken which are shown in FIGS. 4 to 7. As will be appreciated, small diameter catheters have a tendency to drift off the planned trajectory during insertion as a result of the flexibility inherent in a small diameter instrument. Since neurosurgical targets are often deeply situated, typically 70-80 mm from the surface of the skull, and sometimes as much as 100 mm from the skull surface, the catheter must normally be very rigid, and therefore of a larger diameter.

Examples of possible targets include parts of the mesencephalon including the subthalamic nucleus, the substantia nigra and the pedunculor-pontine nucleus. This is a particularly critical region of the brain, where it is important to minimize trauma from the passage of an instrument, which is typically situated about 70-80 mm from the skull surface and contained within a volume which has a height of approximately 20-25 mm.

To facilitate insertion of very fine catheters into mesencephalic targets, insertion takes place as follows.

Firstly, a small diameter tungsten guide wire 22 of 0.6 mm in diameter is inserted in a tube 21 with an outer diameter of 1.7 mm and fixed within the tube 21 with a finger-tightened grub screw 23 such that the wire 22 protrudes from the distal end of the tube 21 by 25 mm. The tube 21 is tapered towards its end for a length of 20 mm. The tube 21 and wire 22 can be seen in FIG. 4 showing the first phase of insertion in which the tube 21 with the wire 22 projecting from its end can be seen.

The finger tightened grub screw 23 can be seen at the top of tube 21, in which the wire 22 is held. Insertion takes place from a stereotactic frame in which the target has been identified and defined in terms of three dimensional coordinates. The stereotactic frame carries a stereoguide which has been modified in order to permit this technique. During the first phase of insertion shown in FIG. 4, the tube and wire are together lowered towards the target. In this case, the tube is 165 mm in length, and since the tube 21 and the wire are inserted as a unit, the distance from the top of the tube to the tip of the guide wire 22 is 190 mm. The wire 22 extends above the top of the tube by approximately 150 mm. The stereoguide includes an upper clamp 24 and a lower clamp 25, and each of these clamps can be swiveled between a position of engagement with the wire or tube which is being inserted or removed, and a position remote from that.

Figure 5:
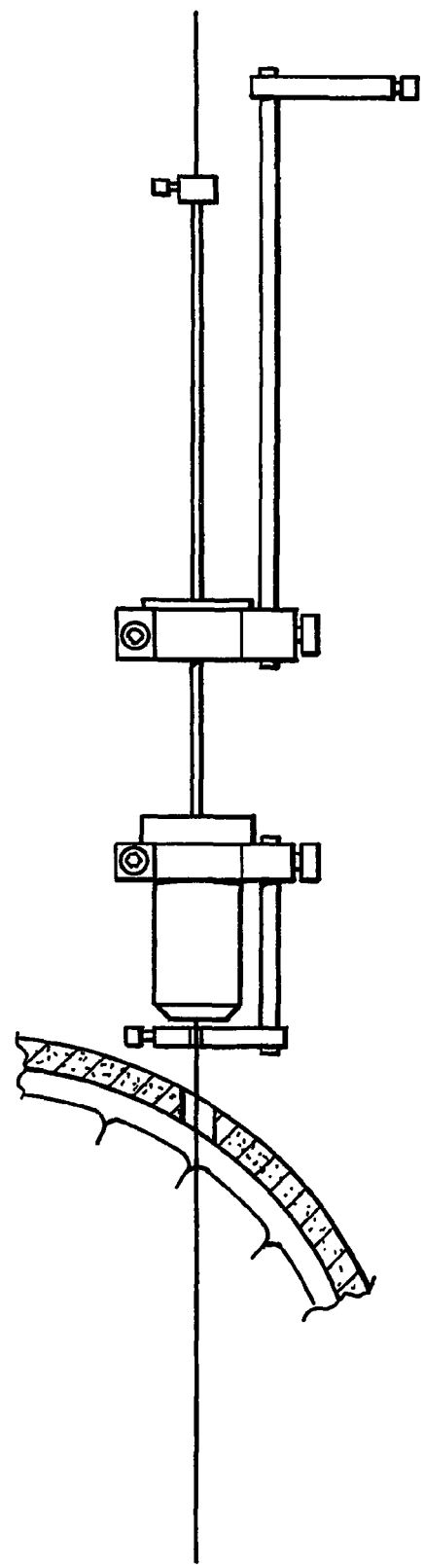
FIG. 5 shows a second phase of stereotactic insertion.
Figure 6:
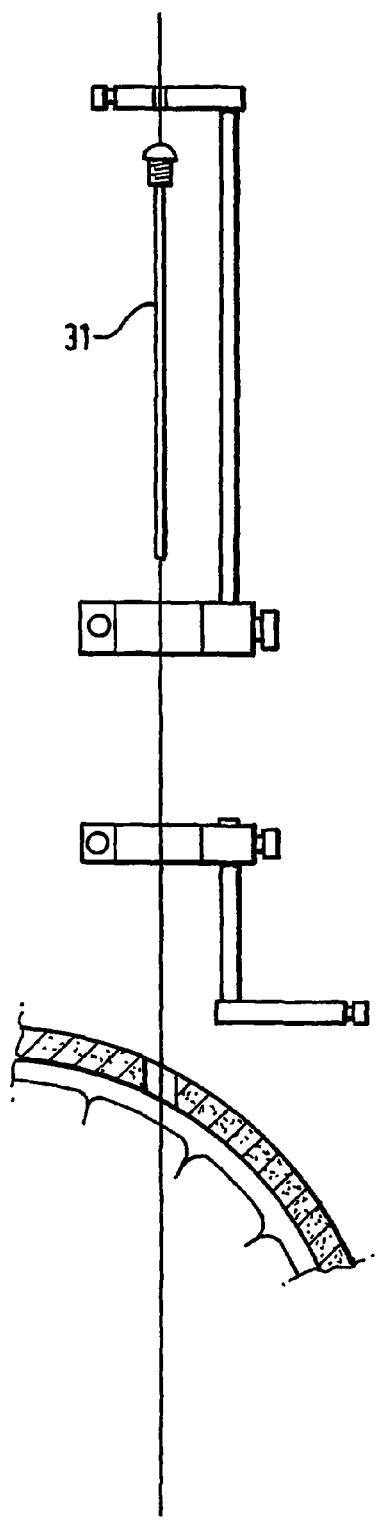
FIG. 6 shows a third phase of stereotactic insertion.

Once the guide wire 22 has reached its target, the upper clamp 24 is swiveled to clamp the proximal end of the guide wire 22. Once the grub screw 23 has been loosened, the tube 21 can be withdrawn from the brain leaving the wire 22 in situ. Once the tube 21 has been raised up towards the upper clamp, the lower clamp can be swung across to clamp the now exposed wire 22, and the upper clamp 24 can be released, as shown in FIG. 5. This allows the tube 21 to be removed altogether from the top of the wire 22.

A guide tube 31 is threaded onto the wire 22, and the upper clamp 24 is then swung around and closed on the wire 22. The lower clamp 25 can then be released to allow the guide tube 31 to be inserted into the brain so that its distance is approximately 1 or 2 cm short of the target, also shown in FIG. 7. The guide tube 32 has at its upper end a head with a threaded outer surface which permits the head to be screwed into the tapped burrhole in the patient's skull, thereby securing the guide tube 31 securely in position. Further features of the head will become clear later in this description.

Figure 7:
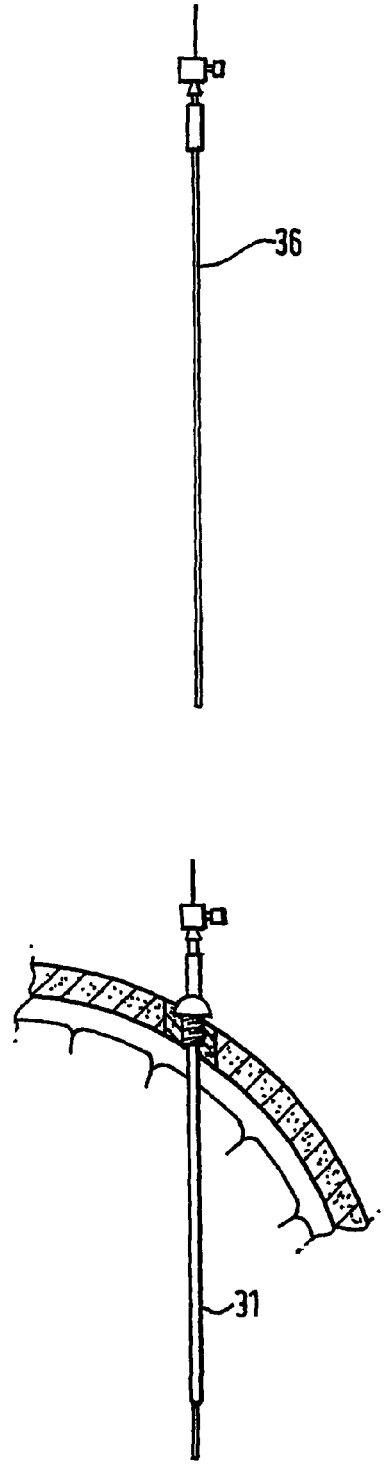
FIG. 7 shows a fourth phase of stereotactic insertion.

Once the guide tube 31 is installed, the guidewire 22 may be removed and FIG. 7 shows that a 0.65 mm catheter 36 can then be inserted down the guide tube 31 to the target.

This method has the particular advantage that, on the first pass, the guide wire being stiffened by the tube 21 will hit the target, and then by inserting a guide tube short of the target, the brain target will be fixed and the guide tube will facilitate the insertion of a very fine instrument to the target. For the treatment of certain conditions such as Alzheimer's disease it is necessary to deliver nerve growth factors to targets in the nucleus basalis through several in-dwelling catheters. If each catheter is only 0.65 mm in diameter, multiple fine catheters can be inserted without substantially disrupting the tissue it is intended to regenerate. In this insertion method, certain diameters of the wire 22, the inside of the tube 21, the outside of the tube 21 and the diameters of the guide tube 31 and the catheter 36 have been referred to. Of course, it will be appreciated that different diameters may be suitable and that the important factor is that the outer diameter of the wire 22 and of the fine catheter 36 which passed through the mesencephalon are as fine as possible, and no larger than 1 mm in cross section. It is preferred that the diameter is no more than 0.7 mm, and even more preferred that it is not more than 0.65 mm.

Figure 8:
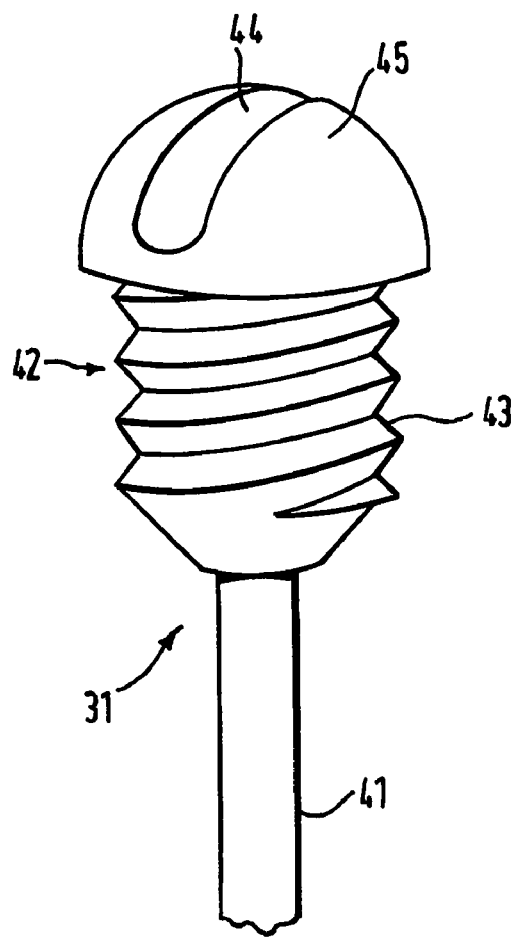
FIG. 8 is a perspective view of a guide tube with a dome-shaped head.
Figure 9:
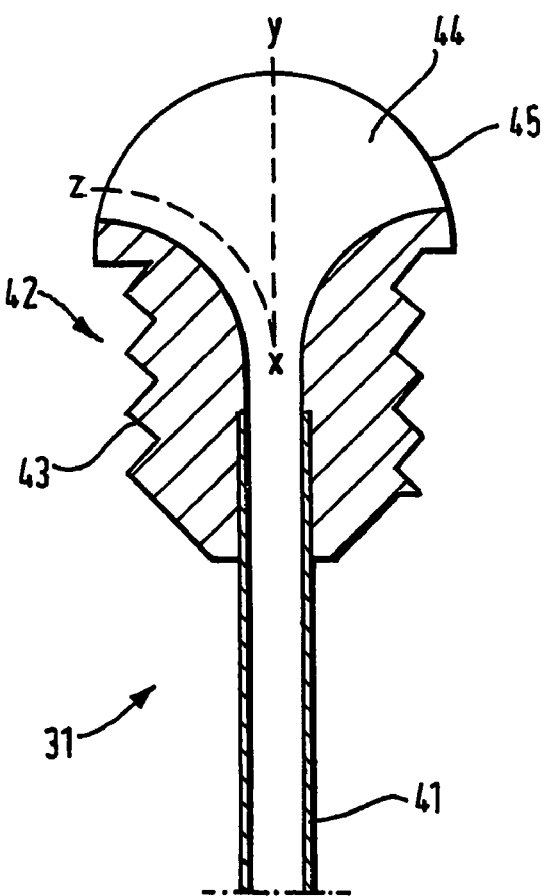
FIG. 9 is a sectional view of the guide tube of FIG. 8 with the dome-shaped head.

The top part of the guide tube 31 is shown in FIGS. 8 and 9 from which it will been seen that the top of the tube 41 carries a head 42 which has a threaded outer surface which can be screwed into the burrhole in the skull through which instruments are inserted. The top of the tube 41 opens into a slot 44 in the head 42. The head 42 is formed with a dome structure 45 in which the slot 44 is located.

As will been seen from FIG. 9, once the head has been secured into the skull, the catheter is located in the tube 41 and is then bent from position small y to position small z. The inner edge around which the catheter is bent is radiused and is shaped in the slot 44 such that the catheter will not kink and such that the distance from x to y is the same as the distance from x to z so that the distal end of the catheter is not moved during the bending process.

It will be understood from FIGS. 8 and 9, that, in this embodiment, the guide tube 31 is formed with the head 42 including the threaded surface 43 and the domed structure 45 as an integral unit.

Figure 10:
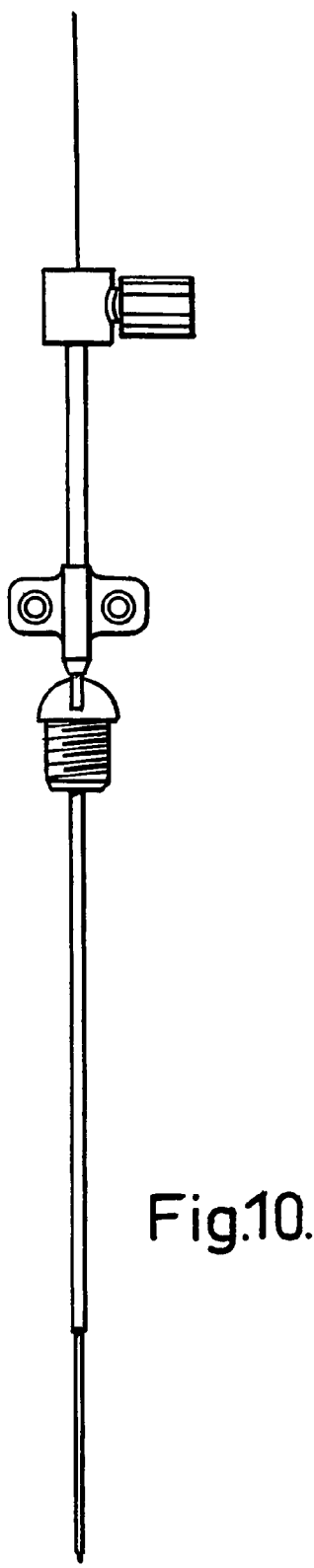
FIG. 10 is a schematic view showing the catheter of FIG. 1 inserted through a guide tube.
Figure 11:
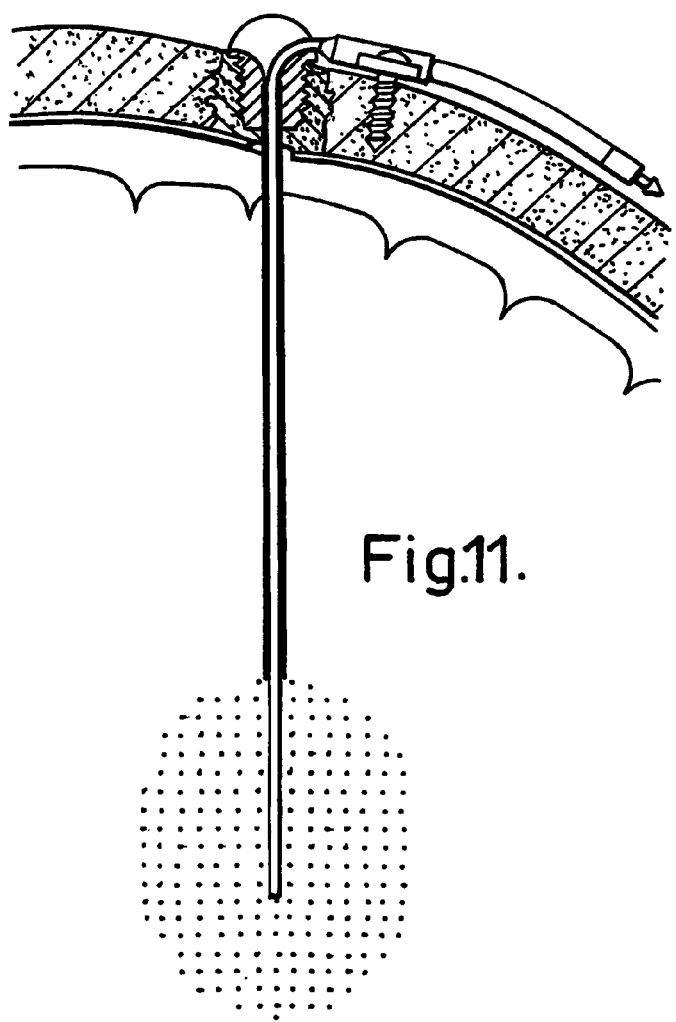
FIG. 11 is a view of the catheter in situ once insertion is complete.

Referring now to FIGS. 10 and 11, it will be seen that a catheter has been inserted into the brain on a stiff wire (not shown) such that the stop 11 abuts the top of the dome structure 45. At this point, the stiff wire is removed and the distal end of the catheter is in the correct position for treatment. The catheter is then bent over to the position shown in FIG. 11 maintaining the stop 11 against the dome structure 45. FIG. 11 also shows how the hub 4 is attached via screws to the skull, and how the connector tubing 3 is directed off towards the pump.

It is preferred that the catheter delivers drugs through a single port at its distal end. This has advantages over catheters with multiple ports at their distal end that may be used for intraparenchymal delivery to the brain. In particular, the use of a single port minimizes the risk of the port becoming obstructed at the low flow rate anticipated for intraparenchymal delivery from the build up of proteinaceous material or gliotic ingrowth. A further advantage of having a single port at the distal end of the intraparenchymal catheter is that it ensures drug delivery at the defined target. The site of drug delivery from a multiport catheter is unpredictable, particularly at low flow rates. This is because flow will be maximal through the port with the lowest resistance. Even though the ports may be of an identical size, the degree to which tissue obstructs any individual port will vary. The net result will be off-axis drug delivery, probably from a single port, which will be sub-optimal for drug delivery to a small target.

Trauma to the brain is minimized upon insertion as a result of using a very fine catheter of no more that 1 mm in diameter and preferably less than 0.7 mm in diameter. In addition, the small diameter catheter makes it suitable for drug delivery to small targets in the brain stem such as the substantia nigra and the pedunculopontine nucleus as well as to other small targets such as the nucleus basalis, the peri-aqueductal grey matter and various thalamic nuclei.

During infusion of a therapeutic substance, the substance flowing from the catheter port or ports will preferably follow the path of least resistance, i.e. flow back along the tissue/catheter interface, up to the cortical surface and then into the CSF compartment. Depending on the flow rate it will defuse variably into the tissues with an ovoid volume of distribution. Containing the drug within a small brain target can therefore be a problem. If, however, the catheter has been inserted into the brain down an indwelling guide tube as in the present invention, then drug exiting the distal port flows back along the tissue/catheter interface until it reaches the guide tube. It then flows preferably along the interface between the guide tube and the catheter and out of the skull into the subgaleal compartment of the scalp. The volume of brain tissue exposed to the drug can therefore be controlled by adjusting the length of the catheter that projects beyond the guide tube as well as adjusting the flow rate. Such fine control is essential if one is to contain delivery of drugs such as neurotrophins within small brain targets.

Example 4

In a trial the intraparenchymal catheter of the present invention was implanted into the brains of five patients with advanced Parkinson's disease via a guide tube, the distal end of which was positioned just short of the desired target. One patient had the catheter implanted unilaterally and four had bilateral implants into the dorsal putamen (i.e. the desired target). Recombinant-methionyl human glial cell line derived neurotrophic factor (r-met Hu GDNF) was chronically infused through the catheters into their dorsal putamen via remotely positioned pumps (8626 Synchromed Pumps, Medtronic Inc, Minneapolis), implanted subcutaneously in the abdominal wall. GDNF is a neurotrophic factor that has been shown to reverse the symptoms of experimentally induced Parkinson's disease in animals. In this trial in humans it was infused at flow rates ranging from 2 to 8, UL per hour and doses between 10.8 and 43.2 micrograms/putamen/day. The patients were assessed preoperatively and at six months using the internationally recognized and validated scoring system for assessing the severity of Parkinson's disease, the Unified Parkinson's Disease Rating Score (UPDRS). At six months there was a 40% improvement in the patients UPDRS scores. The infusions were well tolerated and there were no major side affects.

The invention claimed is:

1. Neurosurgical apparatus comprising:
   a guide tube for insertion into the brain of a patient towards a desired target, the guide tube having distal and proximal ends;
   a head assembly disposed at or in contact with the proximal end of the guide tube, the head assembly having an opening;
   a single fine tube neurosurgical catheter with an external diameter of not more than 0.7 mm for insertion into the brain parenchyma of the patient, the single fine tube neurosurgical catheter being configured to be inserted into the guide tube through the opening in the head assembly; and
   a hub device fixedly secured to the single fine tube neurosurgical catheter, the hub device being non-movably configured with respect to the single fine tube neurosurgical catheter to abut a stopping surface on the head assembly to stop the insertion of the single fine tube neurosurgical catheter in the opening, the hub device thereby allowing the distal end of the single fine tube neurosurgical catheter to be advanced to, stopped and accurately located at the desired target.

2. A method of accurately positioning a catheter at a desired target location in the brain parenchyma of a patient, comprising:
   fixedly securing a hub device to a single fine tube neurosurgical catheter in a manner that the hub device is non-movable with respect to the single fine tube neurosurgical catheter, the single fine tube neurosurgical catheter having an external diameter of 0.7 mm or less;
   inserting a neurosurgical guide into the brain toward the desired target location, the neurosurgical guide including a guide tube having distal and proximal ends,
   stopping the inserting of the neurosurgical guide when the distal end of the guide tube falls short of the desired target by between 5 and 20 mm;
   securing a head assembly to the neurosurgical guide at or in contact with the proximal end of the guide tube, the head assembly having an opening;
   inserting the single fine tube neurosurgical catheter through the opening in the head assembly and through the guide tube;
   advancing the single fine tube neurosurgical catheter such that a distal end of the single fine tube neurosurgical catheter is advanced past the distal end of the guide tube toward the desired target; and
   abutting the hub device against the head assembly to accurately locate the distal end of the single fine tube neurosurgical catheter at the desired target.

* * * * *